United States Patent
Demmer et al.

(10) Patent No.: US 9,504,837 B2
(45) Date of Patent: Nov. 29, 2016

(54) AUTOMATED PHRENIC NERVE STIMULATION AND PACING CAPTURE THRESHOLD TEST

(71) Applicant: Medtronic, Inc., Minneapolis, MN (US)

(72) Inventors: Wade M Demmer, Coon Rapids, MN (US); Todd J Sheldon, North Oakds, MN (US); Robert W Stadler, Shoreview, MN (US); Xusheng Zhang, Shoreview, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 14 days.

(21) Appl. No.: 14/063,766

(22) Filed: Oct. 25, 2013

(65) Prior Publication Data

US 2015/0119950 A1 Apr. 30, 2015

(51) Int. Cl.
*A61N 1/36* (2006.01)
*A61N 1/37* (2006.01)

(52) U.S. Cl.
CPC ............ *A61N 1/3712* (2013.01); *A61N 1/3601* (2013.01); *A61N 1/36114* (2013.01); *A61N 1/371* (2013.01)

(58) Field of Classification Search
CPC ............ A61N 1/371–1/3716; A61N 1/36585; A61N 1/37; A61N 1/3702
See application file for complete search history.

(56) References Cited

U.S. PATENT DOCUMENTS

| | | |
|---|---|---|
| 5,480,414 A | 1/1996 | Markowitz |
| 5,702,427 A | 12/1997 | Ecker |
| 7,225,035 B2 | 5/2007 | Brabec et al. |
| 7,299,093 B2 | 11/2007 | Zhu et al. |
| 7,317,943 B2 | 1/2008 | Ferek-Petric |
| 7,392,086 B2 | 6/2008 | Sathaye |
| 7,792,585 B1 | 9/2010 | Shelchuk |
| 8,185,202 B2 | 5/2012 | Sathaye |
| 8,260,421 B2 | 9/2012 | Sathaye |
| 8,265,736 B2 | 9/2012 | Sathaye et al. |
| 8,326,418 B2 | 12/2012 | Sommer et al. |
| 8,401,639 B2 | 3/2013 | McCabe et al. |
| 8,401,646 B2 | 3/2013 | Stadler et al. |
| 8,527,051 B1 | 9/2013 | Hedberg et al. |
| 8,538,521 B2 | 9/2013 | Zhu et al. |
| 8,565,879 B2 | 10/2013 | Brisben et al. |
| 8,615,297 B2 | 12/2013 | Sathaye et al. |
| 8,649,866 B2 | 2/2014 | Brooke |

(Continued)

FOREIGN PATENT DOCUMENTS

| | | |
|---|---|---|
| EP | 2 514 480 A2 | 10/2012 |
| EP | 2435132 B1 | 8/2013 |

OTHER PUBLICATIONS (PCT/US2014/060929) PCT Notification of Transmittal of the International Search Report and the Written Opinion of the International Searching Authority.

(Continued)

*Primary Examiner* — Joseph Dietrich
(74) *Attorney, Agent, or Firm* — Carol F. Barry

(57) ABSTRACT

A medical device system performs a method for determining pacing threshold data. Signals are received from a cardiac capture sensor and a phrenic nerve stimulation sensor. A cardiac capture threshold is determined from the cardiac capture sensor signal and a phrenic nerve stimulation threshold is determined from the phrenic nerve stimulation sensor signal for multiple pacing electrode vectors.

22 Claims, 6 Drawing Sheets

(56) References Cited

U.S. PATENT DOCUMENTS

| | | |
|---|---|---|
| 2006/0136004 A1 | 6/2006 | Cowan et al. |
| 2006/0241711 A1 | 10/2006 | Sathaye |
| 2007/0066998 A1 | 3/2007 | Hansen et al. |
| 2008/0319500 A1 | 12/2008 | Zhu et al. |
| 2009/0054947 A1 | 2/2009 | Bourn et al. |
| 2009/0210024 A1 | 8/2009 | M. |
| 2010/0305647 A1 | 12/2010 | McCabe et al. |
| 2011/0004264 A1 | 1/2011 | Siejko et al. |
| 2011/0152956 A1 | 6/2011 | Hincapie Ordonez et al. |
| 2011/0196441 A1 | 8/2011 | Ryu et al. |
| 2011/0196442 A1 | 8/2011 | Ryu et al. |
| 2011/0245890 A1 | 10/2011 | Brisben et al. |
| 2012/0035685 A1 | 2/2012 | Saha et al. |
| 2012/0078320 A1 | 3/2012 | Schotzko et al. |
| 2012/0271382 A1 | 10/2012 | Arcot-Krishnamurthy et al. |
| 2012/0296387 A1 | 11/2012 | Zhang et al. |
| 2012/0296388 A1 | 11/2012 | Zhang |
| 2013/0060298 A1 | 3/2013 | Splett et al. |
| 2013/0078320 A1 | 3/2013 | Miller et al. |
| 2013/0197598 A1 | 8/2013 | Schotzko et al. |
| 2013/0253615 A1 | 9/2013 | Arcot-Krishnamurthy et al. |
| 2013/0261471 A1 | 10/2013 | Saha et al. |
| 2013/0261476 A1 | 10/2013 | Rockweiler et al. |
| 2013/0261688 A1 | 10/2013 | Dong et al. |
| 2013/0296961 A1 | 11/2013 | Brooke et al. |
| 2014/0005742 A1 | 1/2014 | Mahajan et al. |
| 2014/0018872 A1 | 1/2014 | Siejko et al. |
| 2015/0231399 A1 | 8/2015 | Demmer et al. |
| 2015/0231400 A1 | 8/2015 | Demmer et al. |

OTHER PUBLICATIONS

C00007237.WOU3 (PCT/US2015/016502) PCT Notification of Transmittal of the International Search Report and Written Opinion of the International Searching Authority.

AUTOMATED PHRENIC NERVE STIMULATION AND PACING CAPTURE THRESHOLD TEST

TECHNICAL FIELD

The disclosure relates to a system and method for performing an automated phrenic nerve stimulation and pacing capture threshold testing in a patient.

BACKGROUND

Multipolar medical electrical leads have been developed for delivering cardiac pacing therapies. Having multiple electrodes along a given heart chamber enables a clinician to select which of the electrodes to use for delivering pacing. Pacing site selection can be critical to achieving a positive clinical benefit from a pacing therapy, such as cardiac resynchronization therapy (CRT). Another consideration taken into account when selecting an electrode for delivering a cardiac pacing therapy is whether or not inadvertent activation of non-cardiac excitable tissue occurs in response to a cardiac pacing pulse. Stimulation of the right or left phrenic nerve may occur when cardiac pacing electrodes are positioned along the right heart chambers or the left heart chambers, respectively in the vicinity of the right or left branch of the phrenic nerve. For example, a quadrapolar lead extending along the left ventricle in a cardiac vein may position one or more electrodes in close enough proximity to the left phrenic nerve that cardiac pacing pulses delivered using the electrodes results in phrenic nerve stimulation (PNS) and diaphragmatic activation.

Testing multiple electrodes in various vector combinations for both cardiac response and other factors such as undesired PNS and hemodynamic response can be a time-consuming task for a clinician and poses a burden on the patient undergoing repeated testing of different vectors while the clinician evaluates various responses. For example, when a left ventricular quadrapolar lead is implanted in a patient, the clinician may test up to sixteen bipolar electrode combinations for pacing capture threshold, hemodynamic response, PNS and other outcomes when selecting which pacing vector should be used for chronic therapy delivery.

SUMMARY

In general, the disclosure is directed towards a medical device system and method for determining pacing threshold data for multiple electrode vectors for use in selecting a pacing therapy delivery vector. In various embodiments, pacing threshold data includes determinations of a presence or absence of PNS during a cardiac pacing capture threshold search and may include determining one or both of a PNS threshold and a cardiac pacing capture threshold.

In one example, a method includes determining a cardiac capture threshold from a cardiac capture sensor signal and detecting phrenic nerve stimulation from a phrenic nerve stimulation sensor signal for multiple pacing electrode vectors. A stimulation pulse is delivered via a selected pacing electrode vector using a first pacing pulse output. PNS, if present, is detected from the PNS sensor signal in response to the first pacing pulse output. The stimulation pulse is adjusted by a first step to a second pacing pulse output in response to detecting the phrenic nerve stimulation. If cardiac capture is detected from the cardiac capture sensor signal in response to the second pacing pulse output, the stimulation pulse output is adjusted by a second step to a third pacing pulse output, the second step being less than the first step.

In another example, a medical device system includes a cardiac capture sensor, a PNS sensor, a pulse generator selectively coupled to multiple electrode vectors, and a processor coupled to the cardiac capture sensor, the PNS sensor and the pulse generator. The processor is configured to control the pulse generator to deliver a stimulation pulse via a selected pacing electrode vector using a first pacing pulse output. If PNS occurs in response to the first pacing pulse output, as determined from the PNS sensor signal, the stimulation pulse is adjusted by a first step to a second pacing pulse output. If cardiac capture occurs in response to the second pacing pulse output, as determined from the cardiac capture sensor, the stimulation pulse output is adjusted by a second step to a third pacing pulse output, the second step being less than the first step.

In another embodiment, a non-transitory computer-readable medium stores instructions that cause a medical device system to perform a method that includes determining a cardiac capture threshold from a cardiac capture sensor signal while detecting PNS from a PNS sensor signal for multiple pacing electrode vectors. A stimulation pulse is delivered via a selected pacing electrode vector using a first pacing pulse output. PNS, if present, is detected from the PNS sensor signal in response to the first pacing pulse output. The stimulation pulse is adjusted by a first step to a second pacing pulse output in response to detecting the phrenic nerve stimulation. If cardiac capture is detected from the cardiac capture sensor signal in response to the second pacing pulse output, the stimulation pulse output is adjusted by a second step to a third pacing pulse output, the second step being less than the first step.

Other embodiments and aspects of a system and method for determining pacing threshold data for multiple electrode vectors are described herein. The details of one or more aspects of the disclosure are set forth in the accompanying drawings and the description below. Other features, objects, and advantages will be apparent from the description and drawings, and from the claims.

DETAILED DESCRIPTION

Figure 1:
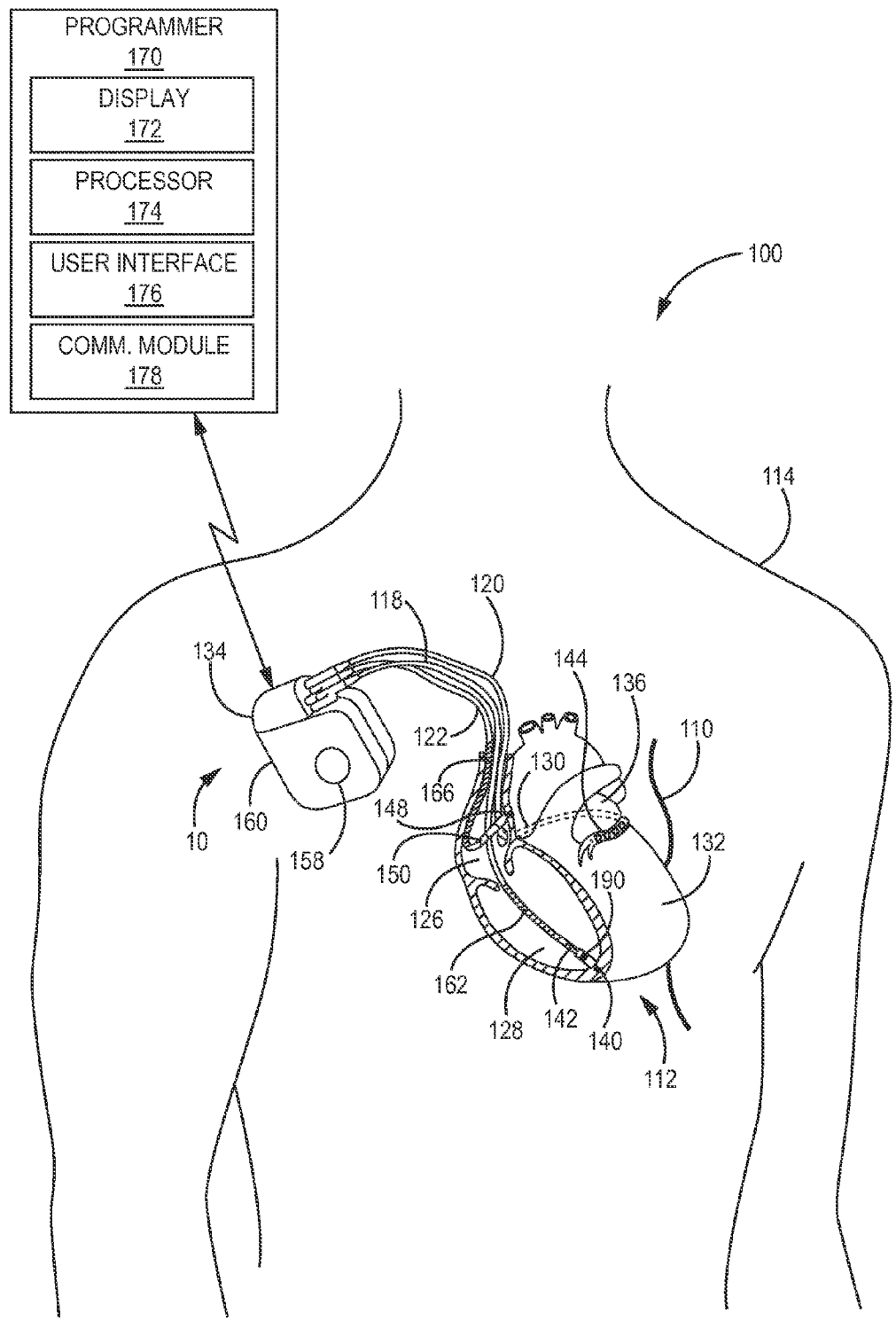
FIG. 1 is a schematic diagram of one embodiment of an implantable medical device (IMD) system in which techniques disclosed herein may be implemented to provide therapy to a heart of a patient.

FIG. 1 is a schematic diagram of one embodiment of an implantable medical device (IMD) system 100 in which techniques disclosed herein may be implemented to provide therapy to heart 112 of patient 114. System 100 is configured to perform testing of multiple electrode vectors for determining pacing threshold data. Pacing threshold data includes data resulting from searching for a cardiac pacing capture threshold while simultaneously detecting whether PNS is occurring. The pacing threshold data may include a cardiac pacing capture threshold or a PNS threshold or both. In addition to pacing threshold data, other cardiac response data, which may include electrical function data, such as conduction times and/or hemodynamic function data, may be acquired while determining the pacing threshold data.

System 100 includes IMD 10 coupled to leads 118, 120, and 122 which carry multiple electrodes. IMD 10 is configured for bidirectional communication with programmer 170. IMD 10 may be, for example, an implantable pacemaker or implantable cardioverter defibrillator (ICD) that provides electrical signals to heart 112 via electrodes coupled to one or more of leads 118, 120, and 122 for pacing, cardioverting and defibrillating the heart 112. IMD 10 is capable of delivering pacing in one or more heart chambers, and in the embodiment shown, is configured for multi-chamber pacing and sensing in the right atrium (RA) 126, the right ventricle (RV) 128, and the left ventricle (LV) 132 using leads 122, 118, and 120, respectively.

IMD 10 delivers RV pacing pulses and senses RV intracardiac electrogram (EGM) signals using RV tip electrode 140 and RV ring electrode 142. RV lead 118 is shown to carry a coil electrode 162 which may be used for delivering high voltage cardioversion or defibrillation shock pulses. IMD 10 senses LV EGM signals and delivers LV pacing pulses using the electrodes 144 carried by a multipolar coronary sinus lead 120, extending through the RA 126 and into a cardiac vein 130 via the coronary sinus. In some embodiments, coronary sinus lead 120 may include electrodes positioned along the left atrium (LA) 136 for sensing left atrial (LA) EGM signals and delivering LA pacing pulses.

IMD 10 senses RA EGM signals and delivers RA pacing pulses using RA lead 122, carrying tip electrode 148 and ring electrode 150. RA lead 122 is shown to be carrying coil electrode 166 which may be positioned along the superior vena cava (SVC) for use in delivering cardioversion/defibrillation shocks. In other embodiments, RV lead 118 carries both the RV coil electrode 162 and the SVC coil electrode 166. IMD 10 may detect tachyarrhythmias of heart 112, such as fibrillation of ventricles 128 and 132, and deliver high voltage cardioversion or defibrillation therapy to heart 112 in the form of electrical shock pulses. Pacing and sensing of the cardiac chambers is typically achieved using the pace/sense electrodes 140, 142, 144, 148 and 150, however in some embodiments coil electrodes 162 and/or 166 may be used in sensing and/or pacing electrode vectors.

While IMD 10 is shown in a right pectoral implant position in FIG. 1, a more typical implant position, particularly when IMD 10 is embodied as an ICD, is a left pectoral implant position. In other embodiments, IMD 10 may be implanted in an abdominal location.

IMD 10 includes internal circuitry for performing the functions attributed to IMD 10 throughout this disclosure. Housing 160 encloses the internal circuitry. The housing 160 or portions thereof may be configured as an active electrode 158 for use in cardioversion/defibrillation shock delivery or used as an indifferent electrode for unipolar pacing or sensing configurations with any electrodes carried by leads 118, 120 and 122. IMD 10 includes a connector block 134 having connector bores for receiving proximal lead connectors of leads 118, 120 and 122. Electrical connection of electrodes carried by leads 118, 120 and 122 and IMD internal circuitry is achieved via various connectors and electrical feedthroughs included in connector block 134.

IMD 10 is configured for delivering CRT by delivering pacing pulses in one or both ventricles 128 and 132 for controlling and improving ventricular synchrony. LV pacing may be delivered using a selected pacing vector that utilizes at least one electrode 144 on multipolar LV lead 120. RV pacing is delivered using RV tip electrode 140 and ring electrode 142 or an alternate indifferent electrode. CRT may be delivered by pacing in a single ventricular chamber (LV or RV) or both chambers (biventricular pacing) depending on patient need. A dual or multi-chamber pacemaker or ICD may deliver pacing pulses to the right and/or left ventricles using programmable pacing pulse timing parameters and selected pacing sites and pacing vectors.

Possible pacing sites for pacing the LV are determined by the locations of electrodes 144. Lead 120 is shown as a quadrapolar lead having four electrodes that can be selected two at a time in at least twelve possible bipolar pacing vectors or selected one at a time with an indifferent electrode, such as housing electrode 158, RV coil electrode 162, or SVC coil electrode 166, in at least four possible unipolar pacing vectors. At least sixteen possible pacing vectors exist, therefore, from which a clinician can select for delivering CRT or other cardiac electrical stimulation therapies. Electrodes 144 positioned along the LV 132 may be in close enough proximity to stimulate the left phrenic nerve 110 and cause inadvertent diaphragm activation. As described herein, a method for rapidly testing for phrenic nerve stimulation (PNS) while simultaneously determining other electrode vector selection parameters such as searching for cardiac pacing capture threshold enables a clinician to efficiently select a pacing vector that avoids PNS or other undesired stimulation.

While a multi-chamber ICD is shown in FIG. 1, it is recognized that techniques disclosed herein may be implemented in a single chamber, dual chamber or multi-chamber pacemaker, with or without anti-arrhythmia therapies such as cardioversion and defibrillation shock capabilities. For example, techniques disclosed herein for detecting PNS while testing other pacing vector selection parameters such as cardiac pacing capture threshold may be used for guiding selection of an electrical stimulation site for any cardiac electrical stimulation therapy.

Furthermore, the techniques disclosed herein may be implemented for detecting other incidental stimulation of excitable tissue that may occur as a side effect during an electrical stimulation therapy, which may be a cardiac therapy or other type of electrical stimulation therapy, such as a neurostimulation therapy. Accordingly, the techniques disclosed herein may be implemented in other medical therapy applications where a capture or activation threshold of a targeted excitable tissue is potentially near enough to a capture or activation threshold of a nearby excitable tissue, potentially resulting in undesired stimulation of the nearby tissue.

Programmer 170 includes a display 172, a processor 174, a user interface 176, and a communication module 178 including wireless telemetry circuitry for communication with IMD 10. In some examples, programmer 170 may be a handheld device or a microprocessor-based home monitor or bedside programming device. A user, such as a physician, technician, nurse or other clinician, may interact with programmer 170 to communicate with IMD 10. For example, the user may interact with programmer 170 via user interface 176 to retrieve currently programmed operating parameters, physiological data collected by IMD 10, or device-related diagnostic information from IMD 10. A user may also interact with programmer 170 to program IMD 10, e.g., select values for operating parameters of the IMD. A user interacting with programmer 170 can initiate threshold data acquisition using the methods disclosed herein. Programmer 170 may receive threshold data from IMD 10 and display the threshold data on display 172. The clinician can then select an electrode vector based on the threshold data and program the selected electrode vector into IMD 10 for therapy delivery.

Examples of communication techniques used by system 100 for programming IMD 10 and retrieving data therefrom include low frequency or radiofrequency (RF) telemetry, which may be an RF link established via Bluetooth, WiFi, or MICS for example. In some examples, programmer 170 may include a programming head that is placed proximate to the patient's body near the IMD 10 implant site, and in other examples programmer 170 and IMD 10 may be configured to communicate using a distance telemetry algorithm and circuitry that does not require the use of a programming head and does not require user intervention to maintain a communication link.

It is contemplated that programmer 170 may be coupled to a communications network via communications module 178 for transferring data to a remote database or computer to allow remote monitoring and management of patient 114 using the techniques described herein. Remote patient management systems, such as CARELINK® available from Medtronic, Inc. Minneapolis, Minn., may be configured to utilize the presently disclosed techniques to enable a clinician to review threshold data, programmed therapy parameters and authorize remote programming of IMD 10.

Figure 2:
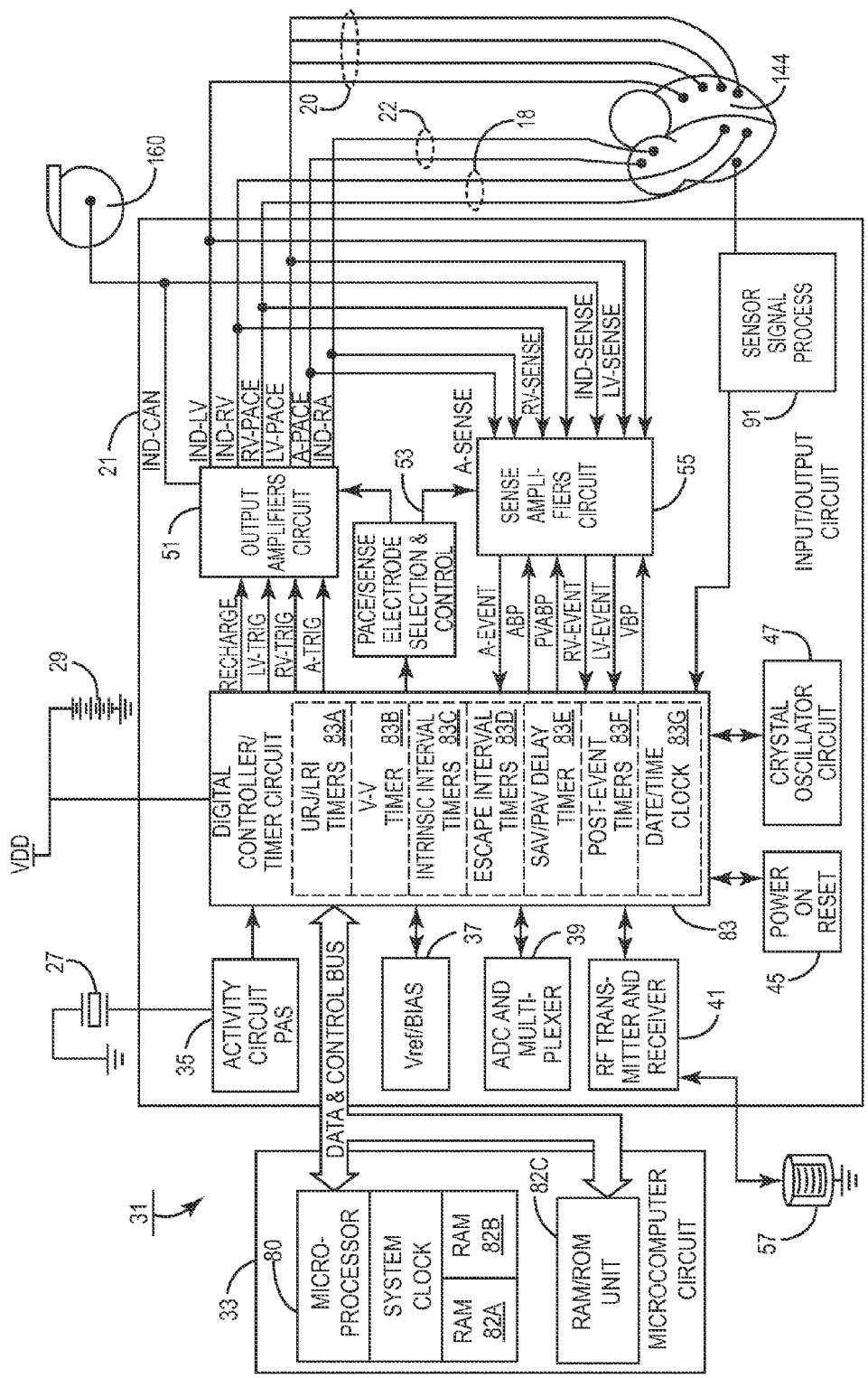
FIG. 2 is a functional block diagram of circuitry included in IMD according to one illustrative embodiment.

FIG. 2 is a functional block diagram of circuitry included in IMD 10 according to one illustrative embodiment. FIG. 2 depicts bipolar RA lead 22, bipolar RV lead 18, and quadrapolar LV CS lead 20 coupled with an implantable pulse generator (IPG) circuit 31 having programmable modes and parameters that may be included in a bi-ventricular DDD/R type of cardiac pacemaker. The IPG circuit 31 is illustrated in a functional block diagram divided generally into a microcomputer 33 and a pacing circuit 21. The pacing circuit 21 includes the digital controller/timer circuit 83, the output amplifiers circuit 51, the sense amplifiers circuit 55, the RF telemetry transceiver 41, the activity sensor circuit 35 as well as a number of other circuits and components described below. The sensor signal processing circuit 91 is coupled to the digital controller/timing circuit 83 and to microcomputer 33 via a data and control bus for use in controlling IMD functions.

Crystal oscillator circuit 89 provides the basic timing clock for the pacing circuit 21, while battery 29 provides power. Power-on-reset circuit 87 responds to initial connection of the circuit to the battery for defining an initial operating condition and similarly, resets the operative state of the device in response to detection of a low battery condition. Voltage reference and bias circuit 37 generates stable voltage reference and currents for the analog circuits within the pacing circuit 21, while analog to digital converter (ADC) and multiplexer circuit 39 digitizes analog signals to provide real time telemetry of cardiac signals, received from sense amplifiers circuit 55, for uplink transmission via RF transmitter and receiver circuit 41. Digitally converted signals from sense amplifiers circuit 55 and/or sensor signal processor 91 may also be used by microcomputer 33 for controlling digital controller/timer circuit 83 according to programmed therapy and/or signal monitoring modes of operation.

The sense amplifiers circuit 55 contains sense amplifiers for atrial and ventricular pacing and sensing. High impedance P-wave and R-wave sense amplifiers may be used to amplify a voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 83 controls sensitivity settings of the atrial and ventricular sense amplifiers 55.

The sense amplifiers 55 are typically uncoupled from the sense electrodes during blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND-CAN electrode 158 from the inputs of the RA sense amplifier (and LA sense amplifier if provided), RV sense amplifier and LV sense amplifier during various blanking periods as described below. The sense amplifiers circuit 55 also includes switching circuits for coupling selected sense electrode lead conductors and the IND-CAN electrode 158 to the RA sense amplifier (and LA sense amplifier if provided), RV sense amplifier and LV sense amplifier. Pace/sense electrode selection and control circuit 53 selects conductors and associated sense electrode pairs to be coupled with the atrial and ventricular sense amplifiers within the sense amplifiers circuit 55 for accomplishing RA, LA, RV and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 83. Similarly, left atrial depolarizations or P-waves in the LA-SENSE signal that are sensed by the LA sense amplifier, if provided, result in a LA-EVENT signal that is communicated to the digital controller/timer circuit 83. Ventricular depolarizations or R-waves in the RV-SENSE signal that are sensed by a ventricular sense amplifier result in an RV-EVENT signal that is communicated to the digital controller/timer circuit 83. Similarly, ventricular depolarizations or R-waves in the LV-SENSE signal that are sensed by a ventricular sense amplifier result in an LV-EVENT signal that is communicated to the digital controller/timer circuit 83. The RV-EVENT, LV-EVENT, and A-EVENT signals may be refractory or non-refractory according to various refractory sensing intervals as described below, and can inadvertently be triggered by electrical noise signals or aberrantly conducted depolarization waves rather than true R-waves or P-waves.

Microcomputer 33 contains a microprocessor 80 and associated system clock and on-processor RAM and ROM chips 82A and 82B, respectively. In addition, microcomputer circuit 33 may include a separate RAM/ROM chip 82C to provide additional memory capacity. Microprocessor 80 normally operates in a reduced power consumption mode and is interrupt driven in some embodiments. In such instances, microprocessor 80 is awakened in response to defined interrupt events, which may include A-TRIG, RV-TRIG, LV-TRIG signals generated by timers in digital timer/controller circuit 83. The A-TRIG, RV-TRIG, and LV-TRIG signals are generated for triggering pacing pulses by output amplifiers circuit 51 upon the expiration of various pacing timing escape intervals before receiving a respective A-EVENT, RV-EVENT, or LV-EVENT signal generated by sense amplifiers circuit 55 upon a sensing threshold crossing of an RA, RV, or LV EGM signal, among others.

The specific values of various intervals and delays timed out by digital controller/timer circuit 83 are controlled by the microcomputer circuit 33 by way of the data and control bus based upon programmed-in therapy control parameter values and operating modes. In addition, if programmed to operate as a rate responsive pacemaker, a timed interrupt, e.g., every cycle or every two seconds, may be provided in order to allow the microprocessor to analyze activity sensor data and update the basic A-A, V-A, or V-V escape intervals used to control pacing pulse delivery in instances that an intrinsic depolarization is not sensed in a respective cardiac chamber, as applicable. In addition, the microprocessor 80 may also serve to define variable, operative AV delay intervals and the energy, e.g. pulse amplitude and pulse width, of each pulse delivered.

Digital controller/timer circuit 83 operates under the general control of the microcomputer 33 to control timing and other functions within the pacing circuit 31 and includes a set of timing and associated logic circuits, not necessarily limited to the certain ones depicted. The depicted timing circuits include URI/LRI timers 83A for timing an upper rate limit interval and a lower rate limit interval for delivering pacing to control the heart rate within the rate limits, a V-V delay timer 83B for controlling a time interval between a ventricular paced or sensed event in ventricle and the time of a paced event in the other ventricle, intrinsic interval timers 83C for timing elapsed V-EVENT to V-EVENT intervals or V-EVENT to A-EVENT intervals or the V-V conduction interval, escape interval timers 83D for timing A-A, V-A, and/or V-V pacing escape intervals, an AV delay interval timer 83E for timing the A-LVp delay (or A-RVp delay) from a preceding A-EVENT or A-TRIG signal, a post-ventricular timer 83F for timing post-ventricular time periods, and a date/time clock 83G.

The AV delay interval timer 83E is loaded with an appropriate delay interval for one ventricular chamber (e.g., either an A-RVp delay or an A-LVp delay as desired) to time-out starting from a preceding A-PACE or A-EVENT. The interval timer 83E triggers pacing pulse delivery upon timing out without any intervening intrinsic sensed event, and can be based on one or more prior cardiac cycles (or from a data set empirically derived for a given patient).

The post-event timer 83F times out various refractory and blanking intervals that are used to control sensing of events associated with intrinsic depolarizations of the heart chambers. Examples of post-ventricular time periods timed by timers 83F may include post-ventricular time periods following an RV-EVENT, LV-EVENT or an RV-TRIG or LV-TRIG and post-atrial time periods following an A-EVENT or A-TRIG. The durations of the post-event time periods may also be selected as programmable parameters stored in the microcomputer 33. The post-ventricular time periods may include a post-ventricular atrial refractory period (PVARP), a ventricular blanking period (VBP), a post-ventricular atrial blanking period (PVABP) and a ventricular refractory period (VRP) although other periods can be suitably defined depending, at least in part, on the operative circuitry employed in the IPG circuit 31. The post-atrial time periods include an atrial refractory period (ARP), a post-atrial ventricular blanking period (PAVBP), and an atrial blanking period (ABP). Generally, during an atrial or ventricular refractory period a sensed A-EVENT or V-EVENT, respectively, is ignored for the purpose of resetting escape intervals but may be counted for other purposes such as determining a heart rate. During an atrial or ventricular blanking period, sensing of an A-EVENT or V-EVENT from a respective EGM signal is typically disabled.

The starting of the post-atrial time periods and the AV delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates AV delays, post-ventricular time periods, and post-atrial time periods that vary with a sensor based escape interval established in response to rate control parameters and/or with the intrinsic atrial rate.

The output amplifiers circuit 51 contains a RA pace pulse generator (and a LA pace pulse generator if LA pacing is provided), a RV pace pulse generator, and a LV pace pulse generator. In order to trigger generation of an RV-PACE or LV-PACE pulse, digital controller/timer circuit 83 generates the RV-TRIG signal at the time-out of the A-RVp delay (in the case of RV pre-excitation) or the LV-TRIG at the time-out of the A-LVp delay (in the case of LV pre-excitation) provided by AV delay interval timer 83E. If biventricular pacing is delivered, a subsequent RV-TRIG (in the case of LV pre-excitation) or LV-TRIG (in the case of RV pre-excitation) is produced upon expiration of the V-V delay timer 83B to pace the second ventricle. Digital controller/timer circuit 83 generates an RA-TRIG signal that triggers output of an RA-PACE pulse (or an LA-TRIG signal that triggers output of an LA-PACE pulse, if provided) at the end of the V-A escape interval timed by escape interval timers 83D.

The output amplifiers circuit 51 includes switching circuits for coupling selected pace electrode pairs from among the lead conductors and the housing electrode 158 to the RA pace pulse generator (and LA pace pulse generator if provided), RV pace pulse generator and LV pace pulse generator. Pace/sense electrode pair selection and control circuit 53 selects lead conductors and associated pace electrode pairs to be coupled with the atrial and ventricular output amplifiers within output amplifiers circuit 51 for accomplishing RA, LA, RV and LV pacing. Furthermore, pace/sense electrode pair selection and control circuit 53 selects pacing vectors for delivering pulses in the LV from the quadrapolar lead 20 by selecting a bipolar or unipolar pacing vector including at least one of electrodes 144. During PNS testing and pacing capture threshold testing, pace/sense electrode pair selection and control circuit 53 selects all sixteen possible pacing vectors or a selected subset of the available sixteen possible pacing vectors for testing as described below.

If IMD 10 is programmed to a rate responsive mode, the signals output by one or more physiologic sensor are employed as a rate control parameter (RCP) to derive a physiologic escape interval used for timing the delivery of pacing pulses. For example, the escape interval is adjusted proportionally to the patient's activity level developed in the patient activity sensor (PAS) circuit 35. The patient activity sensor 27 is coupled to the IPG housing and may take the form of a piezoelectric crystal transducer. The activity sensor output signal is processed and used as the RCP in some examples. Activity sensor 27 generates electrical signals in response to sensed physical activity that are processed by activity circuit 35 and provided to digital controller/timer circuit 83. The illustrative embodiments described herein may also be practiced in non-rate responsive pacemakers.

In some examples, activity sensor 27 is a piezoelectric crystal or other transducer responsive to diaphragmatic activity and generates a signal provided to patient activity circuit 35 that can be used by microprocessor 80 to detect diaphragmatic activation due to PNS resulting from electrical pulses delivered to electrodes 144 (or any of the cardiac electrodes depicted in FIG. 1). An example of an IMD including a sensor for detecting PNS using a piezoelectric transducer or other acoustical sensor is generally disclosed in commonly-assigned pre-grant publication U.S. 2012/0296387 (Zhang, et al.), hereby incorporated herein by reference in its entirety.

IMD 10 may be coupled to other physiological sensors such as oxygenation sensors, pressure sensors, pH sensors, accelerometers, and respiration sensors, for use in providing rate responsive pacing capabilities or for evaluating effects of pacing such as the hemodynamic effects of CRT. Such sensors may be coupled to and analyzed by sensor signal processing circuit 91 to provide information to microcomputer 33 and/or digital controller/timer circuit 83 for use in controlling IMD functions and/or to transmit data to an external programmer 170 via RF transmitter and receiver 41. The patient activity sensor circuit 35 and/or sensor signal processing circuit 91 may receive a signal from a sensor referred to herein as a PNS sensor that is responsive to PNS or diaphragmatic activation. The PAS circuit 35 or the sensor signal processing circuit 91 may provide a PNS signal to microcomputer 33 via the data and control bus for storing PNS data during a cardiac pacing capture threshold test as described herein.

Numerous methods could be implemented for detecting PNS, which may include one or a combination of sensors such as accelerometers, piezo transducers, electrodes, or other sensors producing a signal that changes when PNS occurs.

Such sensors may include respiration sensors since PNS will typically result in a "hiccup" or other respiratory response. A PNS sensor implemented in IMD system 100 may include electrodes for sensing a nerve signal, electromyogram or an impedance signal. For example thoracic impedance may be monitored to detect a change in respiration caused by PNS. Other apparatus and methods that could be implemented for detecting PNS are generally disclosed in commonly-assigned pre-grant U.S. Pub. No. 20130060298 (Splett, et al.) and U.S. Pub. No. 20120078320 (Shotzko, et al.), both of which are hereby incorporated herein by reference in their entirety.

The sense electrodes carried by leads 18, 20 and 22 used for sensing cardiac electrical activity, in the form of cardiac electrogram signals, may be used to detect cardiac capture in response to delivered pacing pulses. Accordingly, sense electrodes are also referred to herein as cardiac capture sensors because the electrogram signals can be used for detecting cardiac capture and loss of capture following a pacing pulse. It is contemplated, however, that alternative sensors may be used for detecting cardiac capture. Methods for detecting cardiac capture are generally disclosed in commonly-assigned U.S. Pat. No. 5,480,414 (Markowitz), U.S. Pat. No. 5,702,427 (Ecker), and U.S. Pat. No. 7,317,943 (Ferek-Petric), all of which patents are hereby incorporated herein by reference in their entirety. The threshold data obtained using techniques described herein, relating to both cardiac capture and PNS for multiple electrode vectors selected from electrodes 144, may be stored in RAM/ROM 82C for transmission to programmer 170 via RF transceiver 41.

Data transmission to and from the external programmer 170 is accomplished by way of the telemetry antenna 57 and an associated RF transceiver 41, which serves both to demodulate received downlink telemetry and to transmit uplink telemetry. Uplink telemetry capabilities will typically include the ability to transmit stored digital information, e.g. operating modes and parameters, cardiac electrogram (EGM) histograms and other events, as well as real time EGM signals of atrial and/or ventricular electrical activity and marker channel data indicating the occurrence of sensed intrinsic depolarizations and pacing pulse delivery in the atrium and ventricles. Real-time and/or stored signals received by other physiological signals including sensor 27 or other sensors listed herein that may be coupled to sensor signal processing circuit 91 and/or data derived from such signals may also be transmitted by transceiver 41.

In one embodiment, microprocessor 80 is a custom microprocessor adapted to fetch and execute instructions stored in RAM/ROM unit 82. It is contemplated, however, that other implementations may be suitable to practice the present invention. For example, an off-the-shelf, commercially available microprocessor or microcontroller, or custom application-specific, hardwired logic, or state-machine type circuit or combinations thereof may perform the functions of microprocessor 80.

The techniques described in this disclosure, including those attributed to the IMD 10 and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry or state machines, as well as any combinations of such components, embodied in IMD 10, programmer 170, such as a physician or patient programmer, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as circuits, modules or units is intended to highlight different functional aspects and does not necessarily imply that such circuits, modules or units must be realized by separate hardware or software components. Rather, functionality associated with one or more circuits, modules or units may be performed by separate hardware or software components, or integrated within common or separate hardware or software components.

When implemented in software, the functionality ascribed to the systems, devices and techniques described in this disclosure may be embodied as non-transitory instructions stored on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

Figure 3:
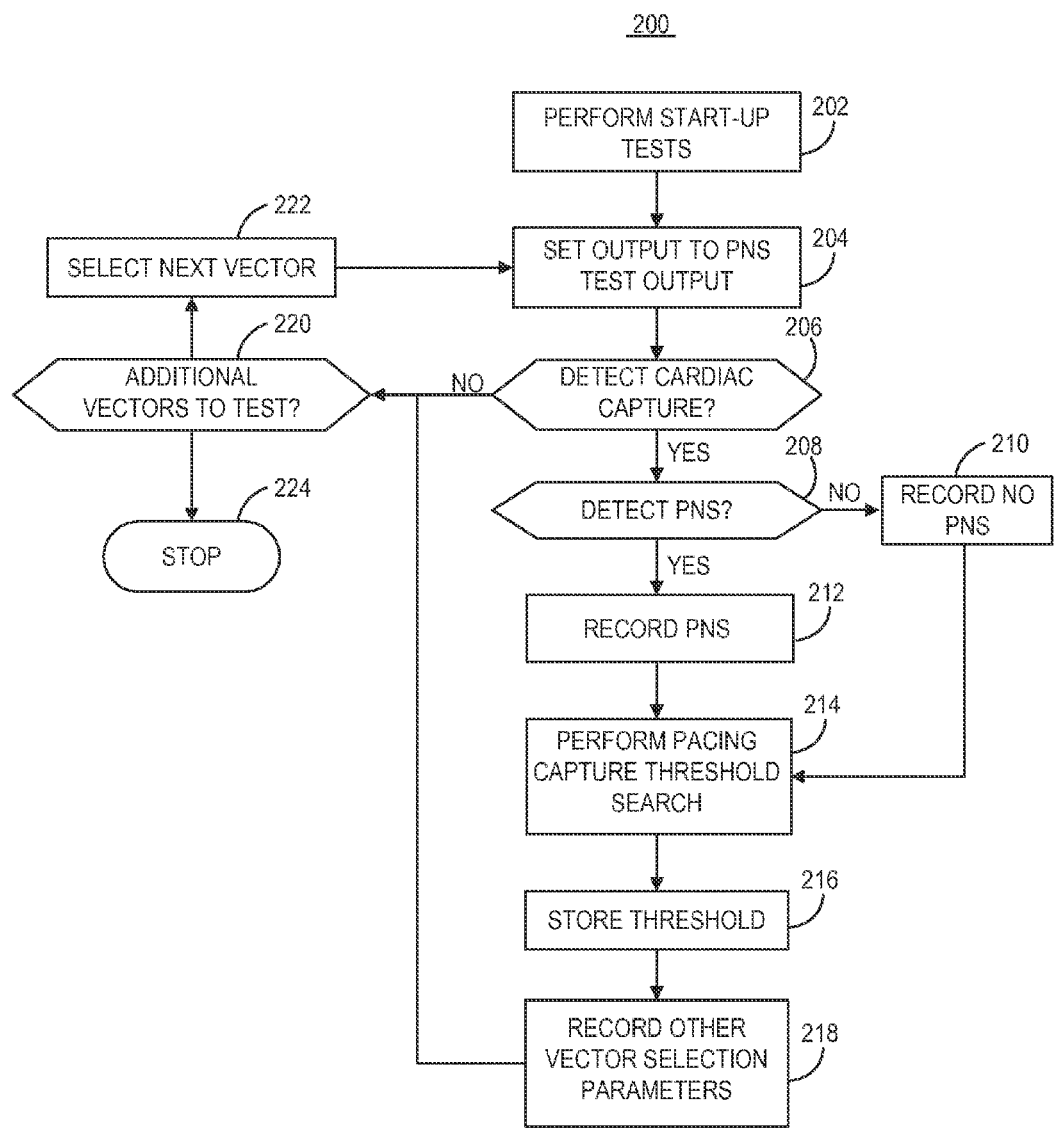
FIG. 3 is a flow chart of a method for testing multiple pacing vectors for PNS and cardiac pacing capture threshold according to one example.

FIG. 3 is a flow chart 200 of a method for testing multiple pacing vectors for PNS and cardiac pacing capture threshold according to one example. The PNS and pacing capture threshold test shown by flow chart 200 and other examples described herein may be performed automatically upon implantation of IMD 10, at any time in response to a command received from programmer 170, automatically on a periodic scheduled basis, or in response to a test trigger. For example, IMD 10 may be configured to monitor lead impedance or automatically detect cardiac pacing loss of capture. If a change in lead impedance is measured by the IMD 10 or loss of cardiac capture occurs, the microcomputer 33 of IMD 10 may trigger a PNS and pacing capture threshold test to be performed to determine if the current pacing vector is still acceptable or to identify a pacing vector for delivering cardiac pacing pulses that produces desirable pacing results.

Other automated triggers for PNS and pacing capture threshold testing may include detection of a change in patient activity or posture. The ability of pacing pulses delivered by cardiac electrodes to stimulate the phrenic nerve and cause diaphragm activation may be posture-dependent or more likely to occur during particular body movements or motions. As such, an activity and/or posture signal may be monitored and used for triggering a PNS and pacing capture threshold test when a change in activity and/or posture is detected or when a particular activity or posture known to make PNS more likely to occur is detected.

For example, a pacing vector may be selected when PNS does not occur at any tested output pulse energy and the vector results in the lowest pacing capture threshold of all tested vectors. Alternatively, a pacing vector may be selected based on a pacing capture threshold below an acceptable margin from a PNS threshold. In other examples, other parameters may be taken into account when selecting a pacing vector besides the cardiac pacing capture threshold and the occurrence of PNS. For example, hemodynamic performance parameters that may be measured from heart sounds, a blood pressure signal, an accelerometer or other physiological signal may be used in combination with threshold data obtained from PNS and pacing capture threshold test results to select an optimal pacing vector. Additionally or alternatively, electrical synchrony parameters such as QRS width, LV-RV conduction time, or other indicators of the electrical synchrony/dyssynchrony of the RV and LV may be used in selecting a pacing vector.

The various examples of PNS and cardiac pacing capture threshold tests are described throughout this disclosure as being performed using a quadrapolar LV lead, such as lead 20 carrying electrodes 144 as shown in FIG. 1. It is contemplated, however, that disclosed systems and techniques may be implemented using any number of electrodes carried by one or more leads positioned in one or more heart chambers. Accordingly, while the illustrative examples described herein refer to tests performed in the LV only, the disclosed methods may be implemented to perform tests in the LV, the RV, the RA or the LA or any combination of heart chambers.

Cardiac pacing capture threshold and PNS information along with any other vector selection parameters can be recorded for each pacing vector tested and provided to a clinician, for example by way of programmer display 172, for making a vector selection that the clinician can program into IMD 10 for delivering pacing pulses. Alternatively, stored information may be used by IMD 10 to automatically select a pacing vector based on cardiac pacing capture threshold, PNS information and optionally any additional vector selection parameters.

Upon initiating a cardiac pacing capture and PNS test, start-up testing is performed at block 202. Start-up testing includes tests or determinations that are considered to be substantially independent of the pacing vectors to be tested. For example, prior to testing vectors for the presence of PNS and pacing capture threshold, it is desirable to verify that the heart rate is stable and within a normal range. Intrinsic A-V and/or V-V conduction times may be measured for establishing pacing escape intervals to be used during the PNS and cardiac pacing capture threshold test to promote pacing pulse delivery prior to intrinsic activity and avoid confounding results due to intrinsic LV depolarizations during the testing.

A cardiac capture sensor signal may be evaluated at block 202 to establish a threshold or template for use in detecting loss of capture. For example, baseline LV EGM signals or thresholds may be established for intrinsic LV electrical activity at block 202 for use in distinguishing between successful LV capture and non-successful LV capture (or loss of capture). A piezoelectric transducer signal or other PNS sensor signal being used to detect the presence of PNS during a cardiac pacing capture threshold search may be recorded to establish a baseline measurement when PNS is known not to be occurring. Baseline PNS sensor signal morphologies or signal features may be determined to establish templates or thresholds for comparing to during the PNS and capture threshold test to distinguish between the presence and absence of PNS.

Accordingly, a number of determinations may be performed at block 202 a single time for use with each pacing vector to be tested. By performing these start-up determinations a single time, the overall time required for determining both PNS data and cardiac pacing capture data for multiple electrode vectors is shortened. A stable heart rate and/or other test condition requirements, a baseline PNS sensor signal representing no PNS, a baseline cardiac capture signal representing loss of capture, and/or other baseline determinations can be made, which will all be applicable to all pacing vectors to be subsequently tested.

At block 204, the output amplifiers circuit 51 is controlled by microcomputer 33 and digital controller/time circuit 83 to deliver a pacing pulse output using a PNS test output, e.g. a predetermined PNS pulse amplitude and/or PNS pulse width. An initial test pacing vector is selected by the pace/sense electrode selection and control 53 to deliver the PNS test pulse output. The PNS test pulse output may be the highest available pulse amplitude or other nominally high pulse amplitude and/or pulse width, e.g. approximately 6 to 8 V pulse amplitude. A relatively high pulse output compared to typical pacing pulse outputs used for therapy delivery is initially tested to determine if PNS is possible at this high level output. If not, use of the pacing vector is considered to be highly unlikely to result in PNS at any cardiac pacing pulse output if the vector is selected for delivering a pacing therapy.

One or more PNS test pulses may be delivered at the PNS test output using a currently selected test electrode vector. An LV EGM signal or other cardiac capture sensor signal is monitored for cardiac capture at block 206. If a predetermined number of pulses delivered at the PNS test output capture the heart, cardiac capture is detected at block 206. At the initial high PNS test energy, cardiac capture is expected to occur.

If cardiac capture does not occur, however, as determined at block 206, the vector is unsuitable for delivering a cardiac stimulation therapy. The lack of cardiac capture may be stored in memory in conjunction with the identity of the selected pacing vector, and the process advances to block 222 where the next pacing vector to be tested is selected by the pace/sense electrode selection and control 53.

If cardiac capture is detected at block 206, a PNS sensor signal is monitored for PNS at block 208. Detection of PNS may be determined from an acoustical or other mechanical sensor signal, electrical sensor, or other sensor signal for which a baseline threshold or signal morphology has been determined corresponding to no PNS. PNS detection may require one or more pacing pulses delivered at the PNS test output. The timing of a pacing pulse during the respiration cycle may affect the PNS threshold for causing phrenic nerve excitation and diaphragm activation. Accordingly, multiple pacing pulses may be delivered over a respiration cycle to determine if any of the pulses cause PNS.

In some examples, a PNS sensor signal is acquired during a window set based on pacing pulse delivery time. The PNS sensor signal is ensemble averaged during the window for multiple pacing cycles over a respiration cycle to determine if the PNS test output causes PNS. For example, PNS detection performed at block 208 may involve analysis of a PNS sensor signal following delivery of two to ten pacing pulses delivered over a respiration cycle.

If PNS is not detected at block 208, the absence of PNS is recorded in conjunction with the current pacing vector identity at block 210. If both cardiac capture and PNS are detected, the presence of PNS at the PNS test output is recorded for the current pacing vector at block 212.

After recording whether PNS is detected for the PNS test output, a pacing capture threshold search is performed at block 214. The pacing capture threshold search may be performed by decreasing the pacing pulse energy from the PNS test output, e.g. decreasing the pulse amplitude or the pulse width, until cardiac capture no longer occurs. The decrement by which the pulse energy is adjusted down from the PNS test output may be equal to at least one pacing safety margin. The pacing safety margin is a margin added to the cardiac pacing capture threshold for setting a cardiac pacing pulse output for safely pacing the heart above the capture threshold but at an energy that does not waste IMD battery charge. For example, a safety margin may be set to 1.5 Volts in one example. As such, the pulse output is decreased by 1.5 Volt steps in one example to search for the pacing capture threshold.

The pacing capture threshold search may alternatively begin at a starting pacing pulse output. The starting pacing pulse output may be a low pulse energy expected to be less than the cardiac capture threshold. The pulse output may be increased until capture is achieved. Alternatively, the starting pacing pulse output may be a mid-point of an expected range of pacing pulse outputs and increased in response to loss of capture or decreased in response to capture being detected. A cardiac pacing capture threshold search may proceed by progressively decreasing from a pacing pulse output that captures the LV, progressively increasing from a pacing pulse output that does not capture the LV, or in any other search pattern such as a binary search pattern starting from a mid-point of a range of pacing pulse output settings.

When searching for the cardiac capture threshold in the method shown in FIG. 3 and in other examples described herein, a single pulse may be delivered at each pulse output step. Alternatively more than one pulse may be delivered to detect cardiac capture at the pulse output setting. When more than one pulse is delivered at a given pulse output setting, a predetermined minimum number of the pulses may be required to capture the heart and otherwise loss of capture is detected if less than the predetermined number of pulses capture the heart. For example, if less than 2 out 3 pulses capture the heart, then loss of capture is detected for the given pulse output and test electrode vector.

In some examples, multiple pulses are delivered at the starting pacing pulse output and at least n out of m pulses are required to capture the heart. If less than the required number of pulses capture, the pulse output will be increased and otherwise the pulse output is decreased according to the search protocol. On subsequently decreased pulse output steps, if the first pulse captures the heart, then the pulse output may be reduced immediately to a next decremented pulse output without requiring n out of m pulses capturing the heart at each step. If the first pulse does not capture, the previous pulse output step is determined as the capture threshold. Alternatively, if the first pulse does not capture additional pulses may be delivered to determine if n out of m pulses capture the heart.

The lowest pulse output that captures the heart according to capture verification criteria implemented in the IMD is determined as the cardiac pacing capture threshold for the given electrode vector. After determining the pacing capture threshold at block 214, the threshold is stored at block 216 for the current pacing vector. During pacing using the current test vector above the determined threshold, other vector selection parameters may be recorded or determined at block 218, e.g. hemodynamic performance parameters, electrical synchrony parameters, or other parameters that a clinician may consider when selecting an optimal pacing vector.

If additional pacing vectors remain to be tested, as determined at block 220, the pace/sense electrode selection and control 53 selects the next test pacing vector at block 222. In some examples, all available pacing vectors, including bipolar and unipolar vectors may be tested. In other examples, a subset of available pacing vectors may be tested. A subset of test vectors may be selected by a clinician, based on lead impedance measurements, or other criteria.

After obtaining threshold information relating to all test vectors, the process is terminated at block 220. The threshold information for some test vectors may be that the cardiac capture threshold exceeds the PNS test output, which may use a maximum available output setting such as a maximum pulse amplitude. The threshold information for other test vectors is the cardiac pacing capture threshold along with whether or not PNS was detected at the PNS test output. In the example shown by flow chart 200, a PNS threshold is not necessarily determined.

Figure 4:
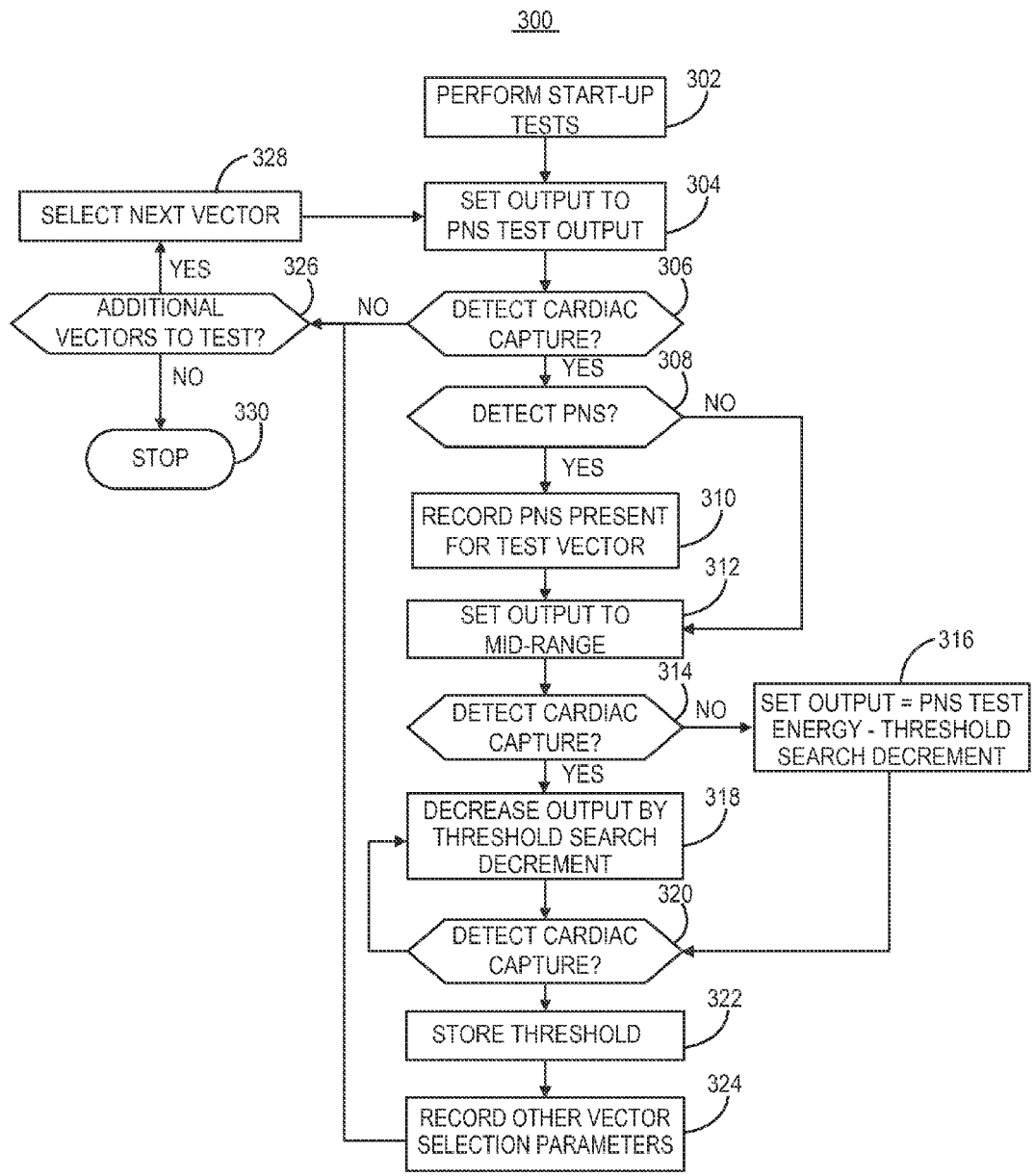
FIG. 4 is a flow chart of a method for determining pacing capture threshold and detecting PNS for multiple pacing vectors according to another embodiment.

FIG. 4 is a flow chart 300 of a method for determining pacing capture threshold and detecting PNS for multiple pacing vectors according to another embodiment. At block 302, start-up tests are performed, such as verifying heart rate, rate stability, and establishing baseline signals of intrinsic heart activity (no capture) and no PNS as described above.

At block 304, the pacing pulse output is set to a PNS test output, typically a high pulse amplitude such as the maximum pulse amplitude available from the IMD 10. If cardiac pacing capture is not detected at block 306 in response to the PNS test output, the vector is not suitable for delivering a cardiac pacing therapy. The process advances to blocks 326 and 328 to select the next test vector if there are additional vectors to be tested.

If cardiac capture is detected in response to the PNS test output at block 306, and PNS is detected at block 308, the presence of PNS for the current test vector is noted in IMD memory at block 310. In some cases, a clinician may only want to know that PNS can occur from a given test vector and that information alone is used to reject the vector for delivering a pacing therapy. In other cases, the knowledge of the presence of PNS at the high PNS test output and the knowledge of the actual cardiac pacing capture threshold provides useful information for selecting a therapy delivery vector. For example, if the cardiac pacing capture threshold is relatively high compared to other electrode vectors, and PNS is present at the PNS test energy, a different pacing vector that has a lower pacing capture threshold and/or no PNS at the PNS test output is selected for therapy delivery.

After storing the presence (or absence) of PNS for the current test vector and verifying cardiac capture, a cardiac pacing capture threshold search is continued at block 312. The pulse energy is adjusted by a first step from the PNS test output to a second pulse output to test for cardiac capture. In one example, the first step adjustment from the PNS test output is a step to the mid-point of the range of available pulse output settings, e.g. to a mid-range pulse amplitude setting. To illustrate, if the maximum pulse output is 8V, and this maximum is used for the PNS test output, the first step adjustment from the PNS test output to a second pulse output may be 4V to set the second pulse output at the mid-range point of the pulse amplitude settings, i.e. 4V, at block 312.

If cardiac capture is not detected at the second pulse output, e.g. the mid-point of the pulse output range, as determined at block 314, the pulse output is increased at block 316. In one example, the pulse amplitude is set equal to the PNS test pulse amplitude less a threshold search decrement. The threshold search decrement may be at least equal to the pacing safety margin in some examples. In other examples, the decrement may be equal to the next lower available pulse amplitude less than the PNS test output or any other pre-defined decrement.

If capture is detected at block 314, the pulse output is decreased from the mid-point of the pulse output range at block 318. After either increasing or decreasing the pulse output as appropriate at block 316 or 318, respectively, the IMD determines if cardiac capture has occurred at block 320. If cardiac capture still occurs, the pulse output is decreased again at block 318 until capture is lost. Accordingly, in some examples, after adjusting the pulse output from the PNS test output by a first step to a second pulse output, the pulse output may be further adjusted by a threshold search step that is less than the first step until cardiac pacing capture is detected.

The lowest pulse output at which capture occurred according to implemented capture verification requirements is stored as the cardiac pacing threshold at block 322. Other electrode vector selection parameters may be determined and stored at block 324 as described previously. If additional vectors remain to be tested, a new vector is selected at block 328, and the process is repeated by returning to block 304. If all test vectors have been tested, the process is terminated at block 330. The PNS information, pacing capture threshold information, and any other electrode selection parameter data obtained for each test vector may be transmitted to an external programmer for display to a clinician and/or used by the IMD to automatically select an electrode vector for therapy.

Figure 5:
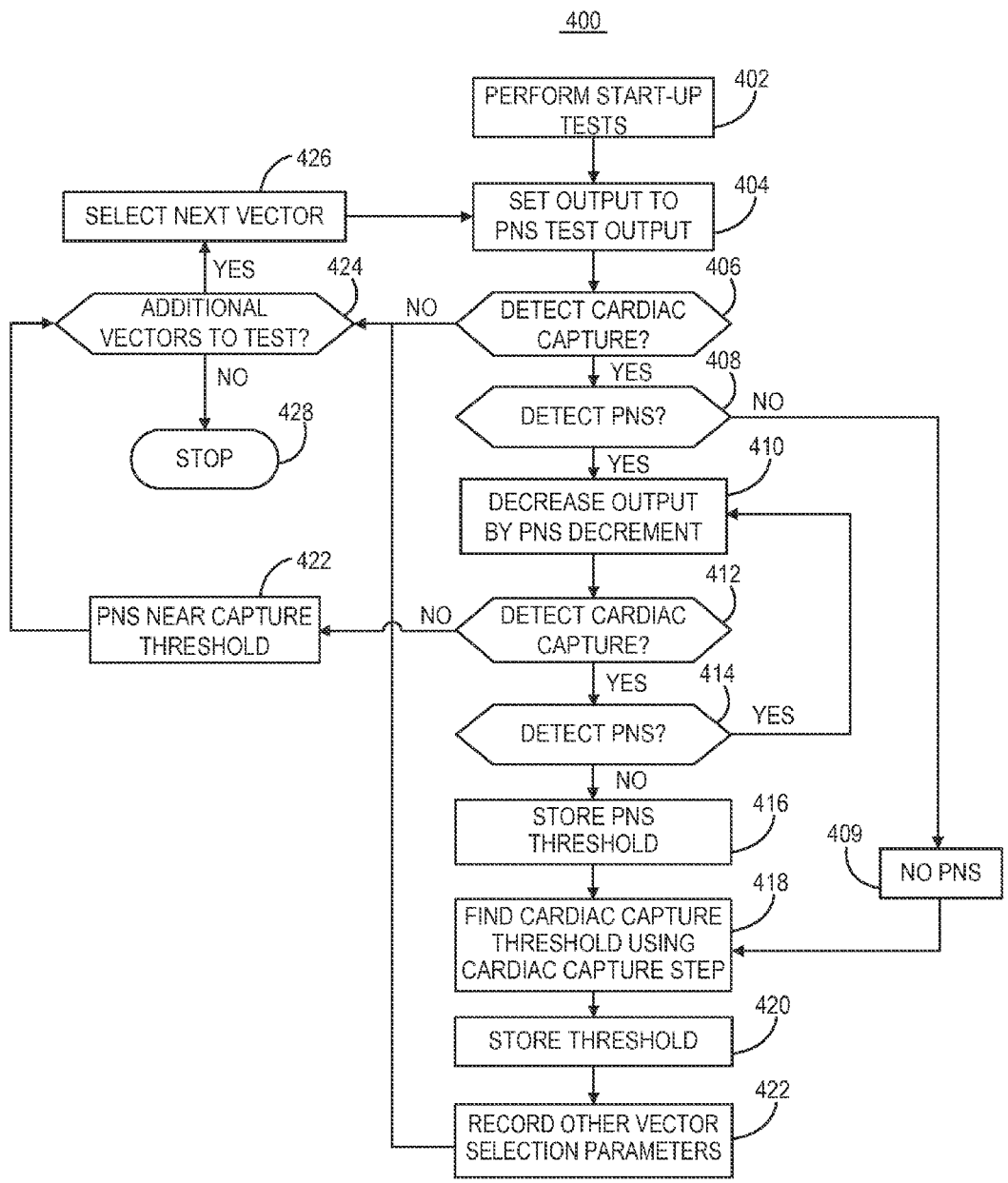
FIG. 5 is a flow chart of a method for determining pacing capture threshold and a PNS threshold for multiple pacing vectors according one embodiment.

FIG. 5 is a flow chart 400 of a method for determining both the cardiac pacing capture threshold and the PNS threshold for multiple pacing vectors according to one embodiment. In some cases, both the PNS threshold and the pacing capture threshold are determined for use in selecting an electrode vector for delivering a cardiac stimulation therapy.

After performing start-up tests at block 402 as described above, one or more output pulses are delivered using an initial test vector at the PNS test output at block 404. If cardiac capture doesn't occur (block 406), the process immediately advances to the next test vector (blocks 424 and 426). If cardiac capture does occur at the PNS test output (block 406), and PNS does not occur (block 408), the absence of PNS is recorded for the current test vector at block 409. A search for the cardiac pacing threshold is continued at block 418 as described below.

If cardiac capture occurs at the PNS test output and PNS is detected (block 408), a search for the PNS threshold is performed by decreasing the pulse output by a PNS threshold search decrement at block 410. This decrement may be relatively larger than an increment/decrement used to search for the cardiac pacing capture threshold. In one embodiment, the PNS threshold search decrement is at least equal to the pacing safety margin. A vector which is capable of causing PNS may be used for delivering a cardiac stimulation therapy if the cardiac pacing capture threshold is more than one safety margin less than the PNS threshold. Accordingly, determining the PNS threshold with a resolution of at least one pacing safety margin enables the vector to be selected for therapy delivery if the cardiac pacing capture threshold is less than one pacing safety margin below the PNS threshold.

Each pulse output level may be tested over at least one full respiration cycle because the PNS threshold may be dependent on timing during the respiration cycle. Testing for the PNS threshold at each pulse output step requires more time than testing for cardiac capture at a given output step since cardiac capture can typically be verified in three pacing pulses or as few as one pacing pulse. By using a relatively larger decrement to search for the PNS threshold, the PNS threshold can be determined more rapidly than if the same decrement is used for both PNS threshold searching and cardiac capture threshold searching.

If cardiac capture is lost at any given pulse output step during the PNS threshold searching, as determined at block 412, the cardiac capture threshold is near or greater than the PNS threshold. This outcome may be stored in memory for the current test vector at block 422. The process moves on to the next test vector at block 426.

As long as cardiac capture continues to be detected at each pulse output, the output is decreased by the PNS threshold search decrement until PNS is no longer detected at block 414. After detecting loss of PNS, the lowest pulse output at which PNS still occurred is stored as the PNS threshold at block 416.

At block 418, adjustments to the pulse output continue as needed until the cardiac pacing capture threshold is found. The adjustments to the pulse output are made using a cardiac capture threshold step, which may be an increment or a decrement depending on the cardiac response to the pulse output.

The first pulse output used at block 414 to continue searching for the cardiac capture threshold after PNS is lost may be the last pulse output used at which PNS was lost but cardiac capture still occurred. The capture threshold search may continue by decreasing the pulse output by a cardiac capture step that is less than the PNS decrement. If cardiac capture still occurred when PNS was lost, the cardiac capture threshold is already known to be at least one PNS decrement, e.g. at least one pacing safety margin, less than the PNS threshold. It may be desirable to know the cardiac pacing threshold with greater resolution than the PNS decrement to allow the pacing therapy output to be set at the lowest level that safely captures the heart above the capture threshold but below the PNS threshold.

In other examples, the first pulse output used at block 418 may be at a mid-point range of the available pulse output values, for example a mid-point of the range of available pulse amplitude settings. The pulse output is increased by the cardiac capture step if cardiac capture is lost at the mid-point range or decreased by the cardiac capture step if cardiac capture is detected at the mid-point range.

In another example, the first pulse output used at block 418 to continue searching for the cardiac pacing capture threshold may be at a mid-way point between 0V or the minimum pulse output setting available and the last pulse output used at block 414 when PNS was lost and cardiac capture still occurred. The pulse output may be adjusted up or down by the cardiac capture step based on the loss or detection of cardiac capture, respectively.

The cardiac capture step may be a fixed step as described above or a variable step such as in a binary search approach. The PNS decrement used in combination with a fixed or variable cardiac capture step may be a fixed amount. Alternatively, instead of using a fixed decrement for performing a downward search from the initial PNS test energy, the PNS threshold search output pulse may be adjusted to a mid-point (or other lower value) of the available output settings, and an upward search may be performed by increasing the output by a PNS increment equal to or greater than the pacing safety margin if PNS is not detected at the mid-point. The amount of time the patient experiences PNS can be reduced by performing an upward search for the PNS threshold rather than a downward search. In other examples, the PNS threshold search may involve variable steps used during a binary search process starting from a desired pulse output.

In any of these variations, at each test output setting used to determine the PNS threshold, cardiac capture is verified such that if cardiac capture is lost during the search for the PNS threshold, a capture threshold that is near (e.g. within a pacing safety margin) or greater than the PNS threshold is identified during the PNS threshold search. Furthermore, the final PNS test output at which cardiac capture still occurs and PNS is lost may guide the selection of the first pacing pulse output to be used at block 418 from which cardiac capture threshold searching continues, using the cardiac capture step for subsequent adjustments of the pulse output for determining the cardiac capture threshold.

Figure 6:
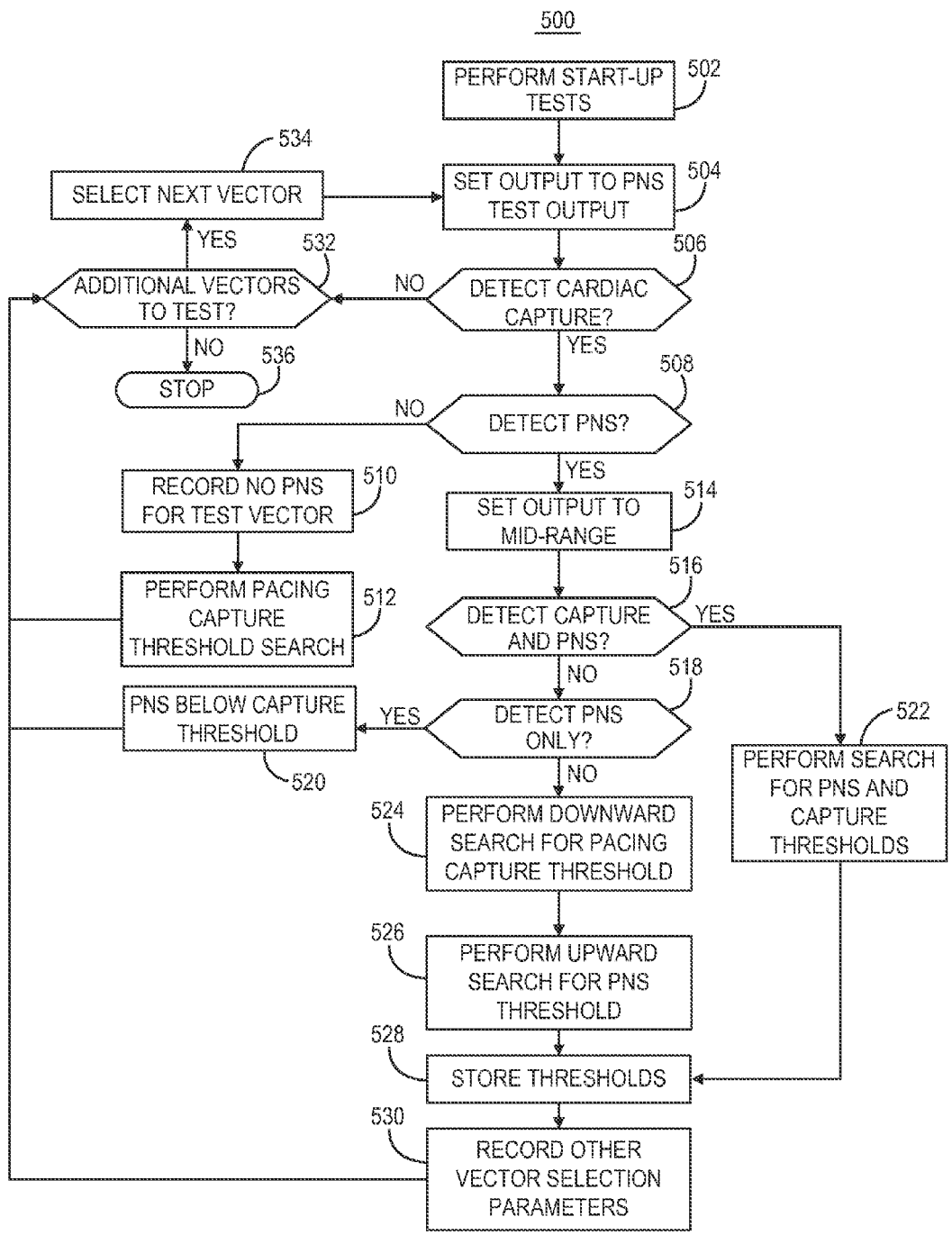
FIG. 6 is a flow chart of a method for performing a test for determining both PNS threshold and pacing capture threshold for multiple electrode vectors.

After determining the cardiac capture threshold, the threshold is stored at block 420. Other vector selection parameters may be determined and stored for the current test vector. If all test vectors have been evaluated, the process stops at block 428. Acquired PNS threshold, cardiac capture threshold and other vector selection parameter data and information may be transmitted to programmer 170 or used by the IMD to automatically select a vector for cardiac stimulation therapy delivery FIG. 6 is a flow chart 500 of a method for performing a test for determining both PNS threshold and pacing capture threshold for multiple electrode vectors. Start-up tests are performed at block 502 as described previously. An output pulse is delivered using the PNS test output and an initial test vector at block 504. If cardiac capture is not detected at the PNS test energy (block 506), which is at or near a maximum pulse output setting as described previously, the process advances to the next test vector (block 534). If cardiac capture is detected, the process advances to determine if PNS is detected at block 508 in response to the PNS test output. The PNS test output may be delivered for multiple pacing pulses over a respiration cycle or at least at over one desired time point or phase in the respiration cycle.

If no PNS is detected at the PNS test output, a cardiac pacing capture threshold search is performed at block 512 using any of the methods described previously or any other desired capture threshold search technique. The cardiac pacing capture threshold is stored in memory with a record indicating that no PNS was detected using the test vector (block 510).

If both cardiac capture and PNS are detected at the initial PNS test output, the process advances to block 514 to search for both the cardiac capture threshold and the PNS threshold simultaneously. In one example, the pulse output is adjusted to a mid-point of a range of pulse output settings, e.g. a mid-range pulse amplitude. If both cardiac capture and PNS are detected in response to the mid-range pulse output, as determined at block 516, the process advances to block 522 where a downward search may continue to determine the PNS and pacing capture threshold. For example, the pulse amplitude may be decreased by a cardiac capture search step until both cardiac capture and PNS are lost. The lowest pulse amplitude at which cardiac capture still occurred is stored as the cardiac capture threshold and the lowest pulse amplitude at which PNS still occurred is stored as the PNS threshold at block 528.

In other embodiments, a binary search may be performed between the mid-range pulse output setting and the minimum pulse output setting. If PNS is lost before cardiac capture, an upward step adjustment may be performed to identify the PNS threshold, which may be equal to half of the previous step adjustment, a step equal to the pacing safety margin or other step size.

If PNS is detected but cardiac capture is not detected in response to the mid-range pulse output at block 518, the PNS threshold is noted to be less than the cardiac pacing capture threshold at block 520. The vector is considered unsuitable for delivering a cardiac stimulation therapy. The process advances to the next test vector at block 534 if additional test vectors are available (block 532).

The other possible outcome to delivering pacing pulses at the second pulse output at block 514, for example at a mid-range setting, is cardiac capture with no PNS, the "no" branch from decision block 518. If this situation occurs, the cardiac pacing capture threshold is less than the mid-range pulse output, and the PNS threshold is greater than the mid-range pulse output. From that point, the search for the two thresholds diverges. A downward search is performed at block 524 for the pacing capture threshold. The search may be performed by decreasing the pulse amplitude by a cardiac capture search step until cardiac capture is lost. Alternatively, a binary or other search technique may be performed.

When searching for the cardiac capture threshold, a single pulse may be delivered at each pulse output. Alternatively more than one pulse may be delivered to verify capture at the pulse output setting with a requirement of a predetermined number of the pulses capturing the heart and otherwise detecting loss of capture as described previously.

An upward search is performed at block 526 to determine the PNS threshold. The upward search may be performed by increasing the pulse output from the mid-range setting by the same step used in the cardiac capture threshold search or by a larger step, e.g. a step equal to or greater than the pacing safety margin. Typically multiple pacing pulses will be delivered at each PNS threshold search step to determine whether PNS occurs at any time during a respiration cycle. The timing of the pacing pulses relative to a respiration cycle is not necessarily known as along as pacing pulses are delivered over an interval of time expected to encompass a respiration cycle. For example at least two pacing pulses are delivered which may be spaced apart more than one cardiac cycle to encompass a greater portion of the respiration cycle. In other examples at least four pacing pulses are delivered at each pulse output step during the PNS threshold search. Some embodiments may include ensemble averaging of the PNS sensor signal following at least four, e.g. eight to twelve, pacing pulses to determine if the averaged PNS sensor signal has deviated from a baseline signal as an indication that PNS occurred at least once during the respiration cycle.

When the cardiac pacing capture threshold search and the PNS capture threshold search are performed simultaneously at block 522 in a generally downward search from the mid-range output setting, multiple pulses may be used at each pulse output step as long as PNS is still being detected. Analysis of the EGM signal for detecting cardiac capture may be performed on one or more of the multiple pulses delivered at a given output. If cardiac capture is detected on the first pulse, or at least a minimum number of pulses delivered at the pulse output step, the remaining pulses need not be evaluated for cardiac capture. Meanwhile, all of the pulses delivered at the given pulse output may be evaluated for PNS detection.

If PNS is no longer being detected and the PNS threshold has been identified, but cardiac capture is still being detected, the search at block 522 may proceed by delivering a fewer number of pulses at each pulse output step. For example, at least four pulses may be delivered at each pulse output step while still searching for the PNS threshold and the cardiac capture threshold, and as few as only one pulse may be delivered at each pulse output step while searching for only the cardiac capture threshold after the PNS threshold has been determined.

In another example, at least eight pulses may be delivered at each pulse output step if neither the PNS nor the cardiac capture threshold have been determined. The PNS sensor signal may be analyzed for all eight or more pacing pulses to determine if PNS occurs over the respiration cycle. A cardiac capture sensor signal may be analyzed for any subset of the pacing pulses delivered at the pulse output step.

After determining the PNS threshold, the number of pacing pulses delivered at each output step may be decreased, e.g. to as low as one pulse at each pulse output step. The pulse output step may initially be larger while both PNS threshold and cardiac capture threshold are being searched for and then decreased after a PNS threshold is determined and the cardiac capture threshold is still being sought. By reducing the number of pulses after determining the PNS threshold, the thresholds for both cardiac pacing capture and PNS can be determined in a time efficient manner.

The thresholds determined at block 522 or at blocks 524 and 526 are stored at block 528 for the current test vector. Other vector selection parameters may be determined and stored at block 530. If any additional electrode vectors remain to be tested, as determined at block 532, the next vector is selected at block 534. Otherwise the process is terminated at block 536. The stored threshold data is used for selecting an electrode vector for delivering a cardiac pacing therapy.

While the embodiments disclosed herein relate to determining threshold data for use in selecting an electrode vector for delivering a cardiac electrical stimulation therapy, it is recognized that the disclosed techniques may be implemented in other electrical stimulation therapy applications. For example, a medical electrical lead carrying multiple electrodes may be positioned for delivering PNS to provide a respiration therapy. In some cases, inadvertent cardiac capture could occur during PNS. As such, the techniques disclosed herein may be utilized to determine cardiac pacing capture threshold and PNS threshold information for use in selecting an electrode vector for PNS that minimizes the likelihood of cardiac capture. Instead of rejecting an electrode vector based on a lack of cardiac capture occurring at an initially high pulse output, an electrode vector that has no cardiac capture at an initially high pulse output would be a desirable vector. When both cardiac capture and PNS occur at the initially high pulse output, additional testing may be performed to acquire threshold data for use in identifying an electrode vector having a PNS threshold sufficiently lower than a cardiac pacing capture threshold to minimize the likelihood of undesired cardiac capture during PNS.

Thus, various embodiments of a system and method for determining cardiac capture and PNS threshold information have been described. One of ordinary skill in the art will appreciate that various modifications may be made to the described embodiments without departing from the scope of the claims. The examples presented herein may be modified, for example by re-ordering various steps or combining or omitting disclosed steps to arrive at other combinations of steps than depicted in the illustrative flow charts presented herein. These and other examples are within the scope of the following claims.

The invention claimed is:

1. An automated method for determining pacing threshold data, comprising:
   receiving a signal from a cardiac capture sensor;
   receiving a signal from a phrenic nerve stimulation sensor;
   determining a cardiac capture threshold from the cardiac capture sensor signal while detecting phrenic nerve stimulation from the phrenic nerve stimulation sensor signal for each of a plurality of pacing electrode vectors, the determining comprising:
      delivering a stimulation pulse via a selected one of the plurality of pacing electrode vectors using a first pacing pulse output;
      detecting from the phrenic nerve stimulation sensor signal whether phrenic nerve stimulation occurs in response to the first pacing pulse output;
      adjusting the stimulation pulse by a first step to a second pacing pulse output in response to detecting the phrenic nerve stimulation;
      detecting from the cardiac capture sensor signal whether cardiac capture occurs in response to the second pacing pulse output; and
      adjusting the stimulation pulse output by a second step to a third pacing pulse output in response to detecting cardiac capture, the second step being less than the first step.

2. The method of claim 1, further comprising:
   delivering a first number of pulses at the first pacing pulse output;
   analyzing the phrenic nerve stimulation sensor signal for each of the first number of pulses for detecting the phrenic nerve stimulation; and
   analyzing the cardiac capture sensor signal for less than the first number of pulses for detecting cardiac capture at the first pacing pulse output.

3. The method of claim 1, further comprising:
delivering a first number of pulses at the second pacing pulse output for detecting whether cardiac capture occurs without phrenic nerve stimulation; and
delivering a second number of pulses at the third pacing pulse output in response to detecting the cardiac capture without phrenic nerve stimulation, the second number of pulses being less than the first number of pulses.

4. The method of claim 1, wherein the first pacing pulse output comprises a maximum output amplitude and the first step is half of an output amplitude range to the second pacing pulse output comprising a mid-range output amplitude.

5. The method of claim 1, wherein the first step is at least a safety pacing margin.

6. The method of claim 1, further comprising:
detecting whether the cardiac capture occurs with phrenic nerve stimulation in response to the second pacing pulse;
repeating adjusting the stimulation pulse by the first step in response to detecting the cardiac capture with phrenic nerve stimulation;
detecting whether the cardiac capture occurs without phrenic nerve stimulation in response to each adjustment to the stimulation pulse; and
adjusting the stimulation pulse by the second step in response to detecting the cardiac capture without phrenic nerve stimulation.

7. The method of claim 1, further comprising:
detecting whether the cardiac capture occurs without phrenic nerve stimulation in response to the second pacing pulse;
repeating adjusting the stimulation pulse by the second step to determine a cardiac capture threshold in response to detecting the cardiac capture without phrenic nerve stimulation; and
adjusting the stimulation pulse upward from the second pacing pulse output to determine a phrenic nerve stimulation threshold in response to detecting the cardiac capture without phrenic nerve stimulation in response to the second pacing pulse.

8. The method of claim 7, wherein the adjusting the stimulation pulse upward from the second pacing pulse output comprises using a third step larger than the second step.

9. The method of claim 1, wherein the first step is to the second pacing pulse output and further comprising:
detecting whether the cardiac capture occurs with phrenic nerve stimulation in response to the second pacing pulse;
repeatedly adjusting the stimulation pulse by the second step in response to detecting the cardiac capture without phrenic nerve stimulation at the second pacing pulse until the cardiac capture threshold is determined; and
repeatedly adjusting the stimulation pulse by a third step in response to detecting the cardiac capture without phrenic nerve stimulation at the second pacing pulse until the phrenic nerve stimulation threshold is determined,
the third step being at least a safety pacing margin and greater than the second step.

10. The method of claim 1, further comprising selecting one of the plurality of electrode vectors for delivering an electrical stimulation therapy in response to the pacing threshold data.

11. A medical device system for determining pacing threshold data, comprising:
a cardiac capture sensor;
a phrenic nerve stimulation sensor;
a pulse generator selectively coupled to a plurality of electrode vectors;
a processor coupled to the cardiac capture sensor, the phrenic nerve stimulation sensor and the pulse generator and configured to determine a cardiac capture threshold from the cardiac capture sensor signal while detecting phrenic nerve stimulation from the phrenic nerve stimulation sensor signal for each of the plurality of pacing electrode vectors, the determining comprising:
controlling the pulse generator to deliver a stimulation pulse via a selected one of the plurality of pacing electrode vectors using a first pacing pulse output;
detecting from the phrenic nerve stimulation sensor signal whether phrenic nerve stimulation occurs in response to the first pacing pulse output;
adjusting the stimulation pulse by a first step to a second pacing pulse output in response to detecting the phrenic nerve stimulation;
detecting from the cardiac capture sensor signal whether cardiac capture occurs in response to the second pacing pulse output; and
adjusting the stimulation pulse output by a second step to a third pacing pulse output in response to detecting cardiac capture, the second step being less than the first step.

12. The system of claim 11, wherein processor is configured to:
control the pulse generator to deliver a first number of pulses at the first pacing pulse output;
analyze the phrenic nerve stimulation sensor signal for each of the first number of pulses for detecting the phrenic nerve stimulation; and
analyze the cardiac capture sensor signal for less than the first number of pulses for detecting cardiac capture at the first pacing pulse output.

13. The system of claim 11, wherein the processor is further configured to:
control the pulse generator to deliver a first number of pulses at the second pacing pulse output for detecting whether cardiac capture occurs without phrenic nerve stimulation and deliver a second number of pulses at the third pacing pulse output in response to detecting the cardiac capture without phrenic nerve stimulation, the second number of pulses being less than the first number of pulses.

14. The system of claim 11, wherein the first pacing pulse output comprises a maximum output amplitude and the first step is half of an output amplitude range to the second pacing pulse output comprising a mid-range output amplitude.

15. The device of claim 11, wherein the first step is at least a safety pacing margin.

16. The system of claim 11, wherein the processor is further configured to:
detect whether the cardiac capture occurs with phrenic nerve stimulation in response to the second pacing pulse;
repeat adjusting the stimulation pulse by the first step in response to detecting the cardiac capture with phrenic nerve stimulation;

detect whether the cardiac capture occurs without phrenic nerve stimulation in response to each adjustment to the stimulation pulse; and adjust the stimulation pulse by the second step in response to detecting the cardiac capture without phrenic nerve stimulation.

17. The system of claim 11, wherein the processor is further configured to:

detect whether the cardiac capture occurs without phrenic nerve stimulation in response to the second pacing pulse;

repeat adjusting the stimulation pulse by the second step to determine a cardiac capture threshold in response to detecting the cardiac capture without phrenic nerve stimulation; and adjust the stimulation pulse upward from the second pacing pulse output to determine a phrenic nerve stimulation threshold in response to detecting the cardiac capture without phrenic nerve stimulation in response to the second pacing pulse.

18. The system of claim 17, wherein the adjusting the stimulation pulse upward from the second pacing pulse output comprises using a third step larger than the second step.

19. The system of claim 11, wherein the first step is to the second pacing pulse output and the processor further configured to:

detect whether the cardiac capture occurs with phrenic nerve stimulation in response to the second pacing pulse;

repeatedly adjust the stimulation pulse by the second step in response to detecting the cardiac capture without phrenic nerve stimulation at the second pacing pulse until the cardiac capture threshold is determined; and repeatedly adjust the stimulation pulse by a third step in response to detecting the cardiac capture without phrenic nerve stimulation at the second pacing pulse until the phrenic nerve stimulation threshold is determined, the third step being at least a safety pacing margin and greater than the second step.

20. The system of claim 11, wherein the processor is further configured to select one of the plurality of electrode vectors for delivering an electrical stimulation therapy in response to the pacing threshold data.

21. A non-transitory, computer-readable storage medium storing instructions for causing a processor included in a medical device system to perform a method for determining pacing threshold data, the method comprising:

receiving a signal from a cardiac capture sensor;

receiving a signal from a phrenic nerve stimulation sensor;

determining a cardiac capture threshold from the cardiac capture sensor signal while detecting phrenic nerve stimulation from the phrenic nerve stimulation sensor signal for each of a plurality of pacing electrode vectors, the determining comprising:

delivering a stimulation pulse via a selected one of the plurality of pacing electrode vectors using a first pacing pulse output;

detecting from the phrenic nerve stimulation sensor signal whether phrenic nerve stimulation occurs in response to the first pacing pulse output;

adjusting the stimulation pulse by a first step to a second pacing pulse output in response to detecting the phrenic nerve stimulation;

detecting from the cardiac capture sensor signal whether cardiac capture occurs in response to the second pacing pulse output; and adjusting the stimulation pulse output by a second step to a third pacing pulse output in response to detecting cardiac capture, the second step being less than the first step.

22. A system, comprising:

receiving means for receiving a signal from a cardiac capture sensor;

receiving means for receiving a signal from a phrenic nerve stimulation sensor;

output means for delivering stimulation pulses; and processing means for determining a cardiac capture threshold from the cardiac capture sensor signal while detecting phrenic nerve stimulation from the phrenic nerve stimulation sensor signal for each of a plurality of pacing electrode vectors, the determining comprising:

delivering a stimulation pulse by the output means via a selected one of the plurality of pacing electrode vectors using a first pacing pulse output;

detecting from the phrenic nerve stimulation sensor signal whether phrenic nerve stimulation occurs in response to the first pacing pulse output;

adjusting the stimulation pulse by a first step to a second pacing pulse output in response to detecting the phrenic nerve stimulation;

detecting from the cardiac capture sensor signal whether cardiac capture occurs in response to the second pacing pulse output; and adjusting the stimulation pulse output by a second step to a third pacing pulse output in response to detecting cardiac capture, the second step being less than the first step.

* * * * *